(12) United States Patent
Saunders

(10) Patent No.: US 11,779,590 B2
(45) Date of Patent: *Oct. 10, 2023

(54) AMP-ACTIVATED PROTEIN KINASE ACTIVATING COMPOUNDS AND USES THEREOF

(71) Applicant: Skylark Bioscience LLC, Clovis, CA (US)

(72) Inventor: Oliver Saunders, Clovis, CA (US)

(73) Assignee: Skylark Bioscience LLC, Clovis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/504,427

(22) Filed: Oct. 18, 2021

(65) Prior Publication Data

US 2022/0133765 A1 May 5, 2022

Related U.S. Application Data

(60) Provisional application No. 63/108,116, filed on Oct. 30, 2020.

(51) Int. Cl.
*A61K 31/7056* (2006.01)

(52) U.S. Cl.
CPC .................. *A61K 31/7056* (2013.01)

(58) Field of Classification Search
CPC .................................................. A61K 31/7056
See application file for complete search history.

(56) References Cited

U.S. PATENT DOCUMENTS

| | | | |
|---|---|---|---|
| 3,355,301 | A | 11/1967 | Huang et al. |
| 4,912,092 | A | 3/1990 | Gruber |
| 5,187,162 | A | 2/1993 | Marangos et al. |
| 5,236,908 | A | 8/1993 | Gruber et al. |
| 5,817,640 | A | 10/1998 | Gruber et al. |
| 7,560,435 | B2 | 7/2009 | Banco et al. |
| 2004/0023901 | A1 | 2/2004 | Cook et al. |
| 2005/0233987 | A1 | 10/2005 | Banco et al. |
| 2009/0124796 | A1 | 5/2009 | Yamakawa et al. |

FOREIGN PATENT DOCUMENTS

| | | |
|---|---|---|
| WO | 9303734 A1 | 3/1993 |
| WO | 00193873 A1 | 12/2001 |
| WO | 0193874 A1 | 12/2001 |
| WO | 0197816 A1 | 12/2001 |
| WO | 0209726 A1 | 2/2002 |

OTHER PUBLICATIONS

Campas, C. et al., Blood, "Acadesine activates AMPK and induces apoptosis in B-cell chronic lymphocytic leukemia cells but not in T lymphocytes", 2003, vol. 101, pp. 3674-3680 (Year: 2003).*
Damasio, Cecil Textbook of Medicine, 20th edition, vol. 2, "Alzheimer's Disease and Related Dementias" (Year: 1997).*
Hardie, D. Grahame et al., Chemistry & Biology, "AMP-Activated Protein Kinase: A Target for Drugs both Ancient and Modern", 2012, vol. 19, pp. 1222-1236 (Year: 2012).*
Maczurek, A et al., Advanced Drug Delivery Reviews, "Lipoic acid as an anti-inflammatory and neuroprotective treatment for Alzheimer's disease", 2008, vol. 60, pp. 1463-1470 (Year: 2008).*
Pradere, U. et al., Chemical Reviews, "Synthesis of Nucleoside Phosphate and Phosphonate Prodrugs", 2014, vol. 114, pp. 9154-9218 (Year: 2014).*
Walters, A. M. et al., Circulation Research, "Mitochondria as a Drug Target in Ischemic Heart Disease and Cardiomyopathy", 2012, vol. 111, pp. 1222-1236 (Year: 2012).*
Zips, D. et al., In Vivo, "New Anticancer Agents: In Vitro and In Vivo Evaluation" 2005, vol. 19, pp. 1-8 (Year: 2005).*
McGuigan, et al., "Design, synthesis and biological evaluation of phosphorodiamidate prodrugs of antiviral and anticancer nucleosides", Eur. J. Med. Chem. 2013, vol. 70, 326-40.
Bookser, et al., "High-Throughput Synthesis of HepDirect Prodrugs of Nucleoside Monophosphates", J. Combinational Chem. 2008, vol. 10(4), 567-72.
Gebeyehu, et al., "Ribavirin, Tiazofurin, and Selenazofurin: Mononucleotides and Nicotinamide Adenine Dinucleotide Analogues. Synthesis, Structure, and Interactions with IMP Dehydrogenase." Journal of Medicinal Chemistry, 1985, vol. 28: 99-105.
McGuigan, et al., "Haloalkyl phosphate derivatives of AZT as inhibitors of HIV: studies in the phosphate region", Antiviral Chemistry and Chemotherapy, 1994, vol. 5(3), pp. 162-168.
CAS RN 2627-69-2, Entered STN: Nov. 16, 1984.
CAS RN 3031-94-5, Entered STN: Nov. 16, 1984.

(Continued)

*Primary Examiner* — Bahar Craigo
(74) *Attorney, Agent, or Firm* — Rimon, P.C.

(57) ABSTRACT

The present invention relates to pharmaceutical compounds, compositions and methods, especially as they relate to the treatment and/or prevention of conditions such as muscle disorders such as polymyositis, dermatomyositis, muscular dystrophy, myasthenia gravis, amyotrophic lateral sclerosis, rhabdomyolysis, and cardiomyopathy, brain disorders including Alzheimer's, stroke, cerebral atrophy, traumatic brain injury, and dementia, aging, diabetes, and cancer, using compounds of Formula (I):

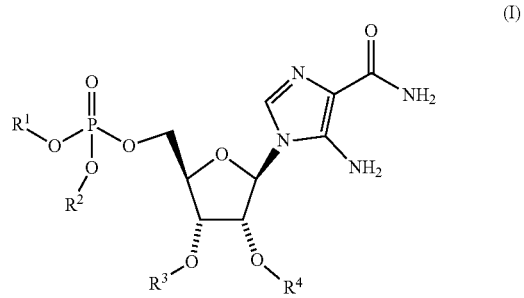

as described herein, including pharmaceutically acceptable salts thereof and pharmaceutical compositions comprising these compounds.

10 Claims, 4 Drawing Sheets

(56) References Cited

OTHER PUBLICATIONS

D.T. Mangano, et al., "Effects of Acadesine on Myocardial Infarction, Stroke, and Death Following Surgery: A Meta-analysis of the 5 International Randomized Trials", Journal American Medical Association 1997, vol. 277, pp. 325-332.
International Search Report dated May 18, 2020, 4 pages.
Written Opinion of the International Searching Authority, dated May 18, 2020, 6 pages.

* cited by examiner

AMP-ACTIVATED PROTEIN KINASE ACTIVATING COMPOUNDS AND USES THEREOF

CROSS-REFERENCE TO RELATED APPLICATIONS

This application claims priority to U.S. Provisional Application No. 63/108,116, filed Oct. 30, 2020; the contents of the applications is incorporated herein by reference in its entirety for all purposes.

FIELD OF THE INVENTION

The field of this invention is compounds, pharmaceutical compositions and methods useful for the treatment of conditions associated with enzymes and pathways regulated by AMP. The compounds, compositions and methods are useful to treat certain cancers, cardiac conditions, diabetic conditions, obesity, and other conditions for which activation of pathways regulated by AMP is beneficial.

BACKGROUND OF THE INVENTION

Acadesine, which is also referred to as 5-amino-1-D-ribofuranosyl-1H-imidazole-4-carboxamide, 5-aminoimidazole-4-carboxamide riboside, AICA riboside and AICAR, is a natural substance with CAS RN 2627-69-2 and with the following formula:

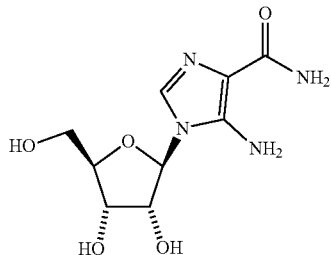

When phosphorylated, AICAR becomes acadesine 5'-monophosphate, which is also called AICAribotide or ZMP, has CAS RN 3031-94-5, which is a natural occurring active metabolite of acadesine, an intermediate in the de novo purine biosynthesis pathway (FIG. 1). ZMP acts in vivo as an AMP mimic. AMP is the monophosphate form of ATP, which is often referred to as the energy currency of a cell: ATP is the most immediate source of energy in cells When ATP is used to provide energy to a cell, such as when a muscle contracts repeatedly, it forms ADP by loss of one phosphate from the triphosphate group. Cellular machinery, e.g., adenylate kinase, normally converts two ADP molecules into one ATP and one AMP: the ATP provides energy to the cell, and the AMP can also be recycled to ATP, but its presence is treated as a sign that the cell needs to make more ATP, see FIG. 2. Many physiological processes other than energy supply are also regulated by AMP: a rise in AMP is interpreted to mean the cell is stressed, as by lack of energy or oxygen. AMP interacts with a number of key intracellular metabolic enzymes. As an indicator of energy stress, AMP directly regulates several vital enzymes within the cell that all function to increase the availability of ATP and improve the cell's ability to maintain energetic balance in the future. These include fructose-1,6-bisphosphatase (FBP1), phosphofructokinase-1 (PFK-1), glycogen phosphorylase (GP), and AMP-activated protein kinase (AMPK). Thus, when the level of AMP in a cell rises above its typical very low concentration, the cell responds by boosting pathways that promote recovery, growth, healing, energy utilization, carbohydrate metabolism, enhanced cellular metabolism, and other beneficial stress responses. AMP promotes cell survival actions that can be beneficial to a human in many ways: it increases mitochondria development, inhibits gluconeogenesis, decreases inflammation, and enhances recycling of damaged proteins.

Work in rodents has demonstrated a vast array of beneficial effects of AICAR, including attenuation of age-related pathology, cognitive decline in dementia, cancer progression, insulin resistance, and functional impairment in several muscular dystrophies. Some of these effects of AICAR presumably occur in part through AMPK activation. However, numerous studies using cells and mice that do not have functional AMPK show that AICAR has many effects that are independent of AMPK. These effects are likely due, at least in part, to ZMP's effects on FBP-1, PFK-1, GP, and perhaps other AMP-sensitive enzymes. Thus the invention provides methods to use ZMP prodrugs for treating such conditions.

Clinical studies in patients undergoing coronary artery bypass graft surgery demonstrate that treatment with acadesine before and during surgery can reduce early cardiac death and myocardial infarction (cf. e.g.: D. T. Mangano, *Journal American Medical Association* 1997, vol. 277, pp. 325-332). Phase III trials have been carried out with acadesine, indicating that it is safe when administered orally and intravenously. There are patents granted and/or patent applications published which relate to the use of acadesine for: preventing tissue damage due to decreased blood flow (cf. U.S. Pat. Nos. 4,912,092, 5,817,640); treating neurodegenerative conditions (cf. U.S. Pat. No. 5,187,162); preventing injury to the central nervous system (cf. U.S. Pat. No. 5,236,908); treating obesity (cf. WO 0193873 A1); treating type 2 diabetes (cf. WO 0197816A1) and treating conditions associated with insulin resistance (cf. WO 0209726 A1). There are patents granted and/or patent applications published which relate to the use of acadesine 5'-monophosphate as flavouring material (cf. U.S. Pat. No. 3,355,301), anticholesteremic/antihyperlipidemic agent (cf. WO 9303734 A1), antiobesity agent (cf. WO 0193874 A1) and antidiabetic agent (cf. WO 0197816 A1). There are also reports describing the use of acadesine, acadesine 5'-monophosphate or prodrugs thereof for treating leukemia and lymphoma. US2005/0233987, U.S. Pat. No. 7,560,435. Furthermore, examples of prodrugs of ZMP and uses thereof are disclosed in WO2020/050935. Most of the biological activities exhibited by ZMP and acadesine are believed to result from mimicking AMP in biochemical pathways that are regulated by AMP.

It is known that acadesine is an apoptosis inhibitor in some types of cells. Thus, for instance, it is known that acadesine inhibits glucocorticoid-induced apoptosis in quiescent thymocytes, that acadesine inhibits apoptosis caused by serum deprivation in fibroblasts overproducing fructose 2,6-bis-phosphate, and that acadesine inhibits ceramide-induced apoptosis in primary astrocytes. Therefore, should acadesine have any effect on lymphocyte apoptosis, acadesine would be expected to be an inhibitor of it.

Throughout the literature on acadesine, the free nucleoside is generally administered, and relatively large dosages are required for efficacy. In most of these studies it is assumed that acadesine is rapidly taken up by cells and phosphorylated by adenosine kinase to the active species ZMP. A number of references also refer to the fact that acadesine is not passively transported and relies upon adenosine nucleoside transporters for cell permeation. If these assumptions about adenosine kinase and the nucleoside transporters are true, then the use of acadesine to produce the active species ZMP has two problems. The first problem is that adenosine kinase is not expressed in equal amounts in every cell type, and dosing of acadesine will produce vastly different amounts of ZMP in different tissues.

The second problem with acadesine is the hydrophilic structure of the molecule. AICAR has very low bioavailability when dosed orally, because most of the administered compound is excreted unaltered in urine. This makes the preferred method of dosing intravenous injection or infusion. Intravenous administration of AICAR runs into other problems not taken into account in the animal and human trials to date. Adenosine, when dosed IV, has a half-life of around 12 seconds. This property is due to the need to closely control extracellular adenosine levels. Bolus doses of adenosine are taken up into erythrocytes and endothelial cells proximal to the location of IV administration very rapidly. It can be assumed that a majority of acadesine given IV is likewise taken up by red blood cells and endothelial cells and is rapidly phosphorylated in those cells to the active metabolite ZMP. Thus delivery to cells in tissues other than blood, such as brain and muscle, is predicted to be very inefficient.

Acadesine, once inside a cell and phosphorylated to ZMP, is ion-trapped inside the cell. ZMP will thus accumulate inside red blood cells and endothelial cells until it causes toxicity, rather than reaching other cell types where it may be needed. Therefore, IV administration of large doses of the nucleoside acadesine will produce very small systemic exposure of the active species ZMP, along with toxic effects in RBCs and endothelial cells.

In order to achieve a desired therapeutic effect, however, it is typically necessary to deliver an active agent in a form that reaches other tissues where its effect is likely to be pharmaceutically beneficial rather than entering the first available cell. The present invention provides compounds of Formula (I) that, without being bound by theory, are believed to act as prodrugs of ZMP, and are not rapidly internalized and trapped by the first cell they encounter as AICAR may be, but are instead available systemically.

Once a compound of Formula (I) enters a cell, the prodrug moiety is cleaved, generating the active species ZMP. Accordingly, the compounds of Formula (I) provide greater systemic bioavailability of the active metabolite ZMP than AICAR itself does, while also reducing adverse effects associated with quick entry into other cells, particularly red blood cells, that can be adversely affected by AICAR when it is administered intravenously. These compounds of Formula (I) are thus useful to treat conditions treatable with acadesine or ZMP, but require lower doses to be effective. Other features and advantages of the prodrugs of the invention, as well as methods of using them, will be appreciated in view of the following detailed descriptions.

DISCLOSURE OF THE INVENTION

The present invention relates to compounds of Formula (I), pharmaceutical compositions comprising these compounds, and methods to use these compounds and pharmaceutical compositions. In particular, the invention provides methods to use the compounds of the invention for treating disorders in brain and muscle tissues and the liver.

In one aspect, the present disclosure provides a heterocyclic compound having a structure according to Formula (I):

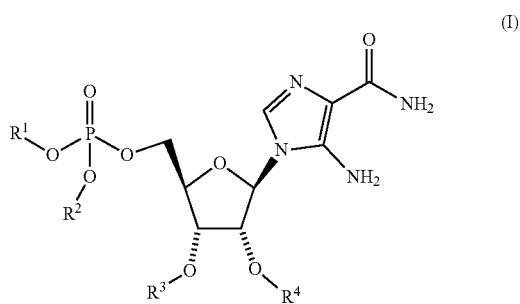

wherein
  $R^1$ is selected from:
    (a) $C_1$-$C_6$ alkyl substituted with one or more groups selected from list X;
    (b) Q; and
    (c) -L-Q;
  $R^2$ is selected from:
    (a) $C_1$-$C_6$ alkyl substituted with one or more groups selected from List X;
    (b) Q;
    (c) -L-Q; and
    (d) H;
    Q is independently selected at each occurrence and represents a ring selected from phenyl and a 5-6 membered heteroaryl containing one to three heteroatoms selected from N, O and S as ring members, and each Q is optionally substituted with one to three groups selected from List M;
    L is $C_1$-$C_4$ alkylene optionally substituted with one or two groups selected from halo, oxo (=O), —OH, $C_1$-$C_2$ haloalkyl, $C_1$-$C_2$ alkoxy, $C_1$-$C_2$ haloalkoxy, CN, COOR$^7$, —OC(=O)R$^7$, and NR$^8$R$^9$;
  $R^3$ is H or —C(=O)—R$^6$.
  $R^4$ is H or —C(=O)—R$^6$.
  $R^6$ is H or $C_1$-$C_6$ alkyl that is optionally substituted with one to three groups selected from halo, CN, hydroxy, $C_1$-$C_4$ alkoxy, $C_1$-$C_4$ haloalkyl, —NR$^8$R$^9$, —OC(=O)—R$^7$, and COOR$^7$;
  $R^7$ is independently selected at each occurrence from H and $C_1$-$C_6$ alkyl optionally substituted with up to three groups selected from halo, CN, hydroxy, $C_1$-$C_4$ alkoxy, and $C_1$-$C_4$ haloalkyl;
  $R^8$ and $R^9$ are each independently selected at each occurrence from H and $C_1$-$C_4$ alkyl optionally substituted with one or two groups selected from List X;
    or $R^8$ and $R^9$ taken together with the Nitrogen to which both are attached form a 5-6 membered heterocyclic ring optionally containing an additional heteroatom selected from N, O and S as a ring member, and optionally substituted with one to four groups selected from halo, oxo, $C_1$-$C_2$ alkyl, hydroxy, $C_1$-$C_2$ alkoxy, CN, and COOR$^7$;
  $R^{10}$ is independently at each occurrence $C_1$-$C_6$ alkyl optionally substituted with up to three groups selected from halo, CN, hydroxy, $C_1$-$C_4$ alkoxy, and $C_1$-$C_4$ haloalkyl;
  List X consists of halo, CN, —OH, $C_1$-$C_4$ alkoxy, $C_1$-$C_4$ haloalkyl, $C_1$-$C_4$ haloalkoxy, =O, —COOR$^7$, —OC(=O)R$^7$, —O—COOR$^{10}$, —SO$_2$R$^{10}$, —SO$_2$NR$^8$R$^9$, -O-Q, and -O-L-Q;

List M consists of halo, CN, $NO_2$, $COOR^7$, $CONR^9R^9$, $-SO_2R^{10}$, $-SO_2NR^8R^9$, $C_1$-$C_2$ haloalkyl, $C_1$-$C_2$ haloalkoxy, $C_1$-$C_2$ alkoxy, and $C_1$-$C_2$ alkyl;

or a pharmaceutically acceptable salt thereof.

In particular, the invention provides a compound selected from:

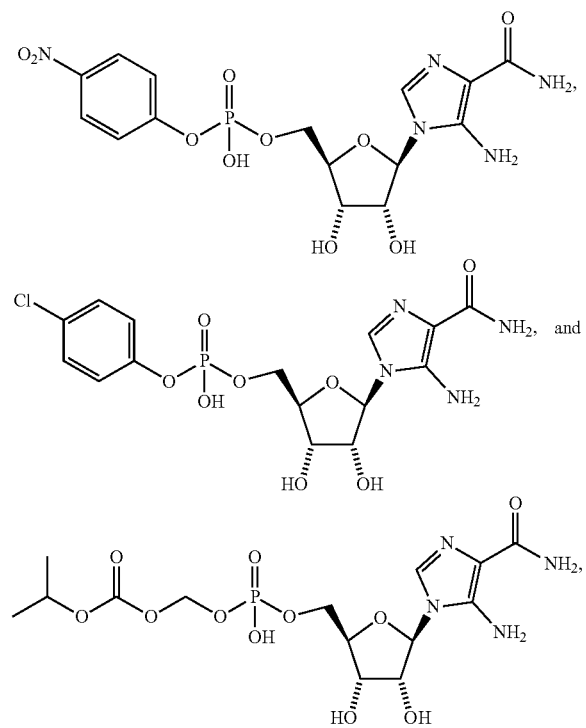

for use in treating indications as disclosed herein, especially disorders in the muscle, brain and liver tissues, and for preparation of medicements useful to treat such indications.

The compounds of Formula (I) can be used to treat a condition for which an AMP mimic is beneficial, especially in tissues other than blood, e.g., disorders in the muscles, brain and liver that are driven by biochemical pathways that are regulated by AMP. As prodrugs of acadesine monophosphate, the compounds of Formula (I) exhibit enhanced intracellular efficacy and systemicity compared to AICAR or ZMP, and provide enhanced systemic delivery of ZMP. Thus the compounds of Formula (I) are useful to treat conditions in which AICAR and/or ZMP are effective, and are more effective because the active agent is not disproportionally trapped in blood cells. These conditions include muscle disorders such as polymyositis, dermatomyositis, muscular dystrophy, myasthenia gravis, amyotrophic lateral sclerosis, rhabdomyolysis, and cardiomyopathy, brain disorders including Alzheimer's, stroke, cerebral atrophy, traumatic brain injury, and dementia, aging, diabetes, and cancers. While AICAR or ZMP has been reported to be useful to treat acute lymphoblastic leukemia, B-cell chronic lymphocytic leukemia (B-CLL), type 2 diabetes, cardiac damage, and myocardial infarction, other B-cell lymphoproliferative disorders including splenic marginal zone lymphoma, mantle cell lymphoma, follicular lymphoma, lymphoplasmacytic lymphoma, and Waldenström syndrome, and to protect against ischemic injury during cardiac surgery, the invention provides methods to use the compounds of Formula (I), including pharmaceutically acceptable salts thereof, to treat muscle disorders such as polymyositis, dermatomyositis, muscular dystrophy, myasthenia gravis, amyotrophic lateral sclerosis, rhabdomyolysis, and cardiomyopathy, brain disorders including Alzheimer's, stroke, cerebral atrophy, traumatic brain injury, and dementia, aging, diabetes, and cancers In one aspect, the invention provides compounds of Formula (I) as described herein and their pharmaceutically acceptable salts for treatment of the conditions mentioned above.

In some embodiments, the compounds described herein can be used in therapy, particularly to treat conditions mentioned above in subjects in need of therapy for these conditions.

In another aspect, the present disclosure provides a pharmaceutical composition comprising a compound of Formula (I) as described herein admixed with at least one pharmaceutically acceptable carrier or excipient to treat muscle disorders such as polymyositis, dermatomyositis, muscular dystrophy, myasthenia gravis, amyotrophic lateral sclerosis, rhabdomyolysis, and cardiomyopathy, brain disorders including Alzheimer's, stroke, cerebral atrophy, traumatic brain injury, and dementia, aging, diabetes, and cancers.

In yet another aspect, the disclosure provides a method for treating and/or preventing conditions associated with insufficient activity of an AMP-regulated enzyme or pathway such as fructose-1,6-bisphosphatase, glycogen phosphorylase, phosphofructokinase-1, and AMPK. including muscle disorders such as polymyositis, dermatomyositis, muscular dystrophy, myasthenia gravis, amyotrophic lateral sclerosis, rhabdomyolysis, and cardiomyopathy, brain disorders including Alzheimer's, stroke, cerebral atrophy, traumatic brain injury, and dementia, aging, diabetes, and cancers.

In yet another aspect, the present disclosure provides for a use of a compound of Formula (I) as described herein for the manufacture of a medicament. In particular, the compounds are useful for manufacture of a medicament for treating conditions such as muscle disorders such as polymyositis, dermatomyositis, muscular dystrophy, myasthenia gravis, amyotrophic lateral sclerosis, rhabdomyolysis, and cardiomyopathy, brain disorders including Alzheimer's, stroke, cerebral atrophy, traumatic brain injury, and dementia, aging, diabetes, and cancers.

In yet another aspect, the present disclosure provides a combination for treating and/or preventing a condition for which AICAR and/or ZMP have efficacy, including those mentioned above. The combination comprises a compound of Formula (I) as described herein, and at least one additional therapeutic agent useful for treating the same subject to be treated with the compound of Formula (I), e.g., a subject having muscle disorders such as polymyositis, dermatomyositis, muscular dystrophy, myasthenia gravis, amyotrophic lateral sclerosis, rhabdomyolysis, and cardiomyopathy, brain disorders including Alzheimer's, stroke, cerebral atrophy, traumatic brain injury, and dementia, aging, diabetes, or cancer.

In yet another aspect, the present disclosure provides a method for providing enhanced activation of PFK-1, FBP1, or GP.

DETAILED DESCRIPTION

Figure 1:
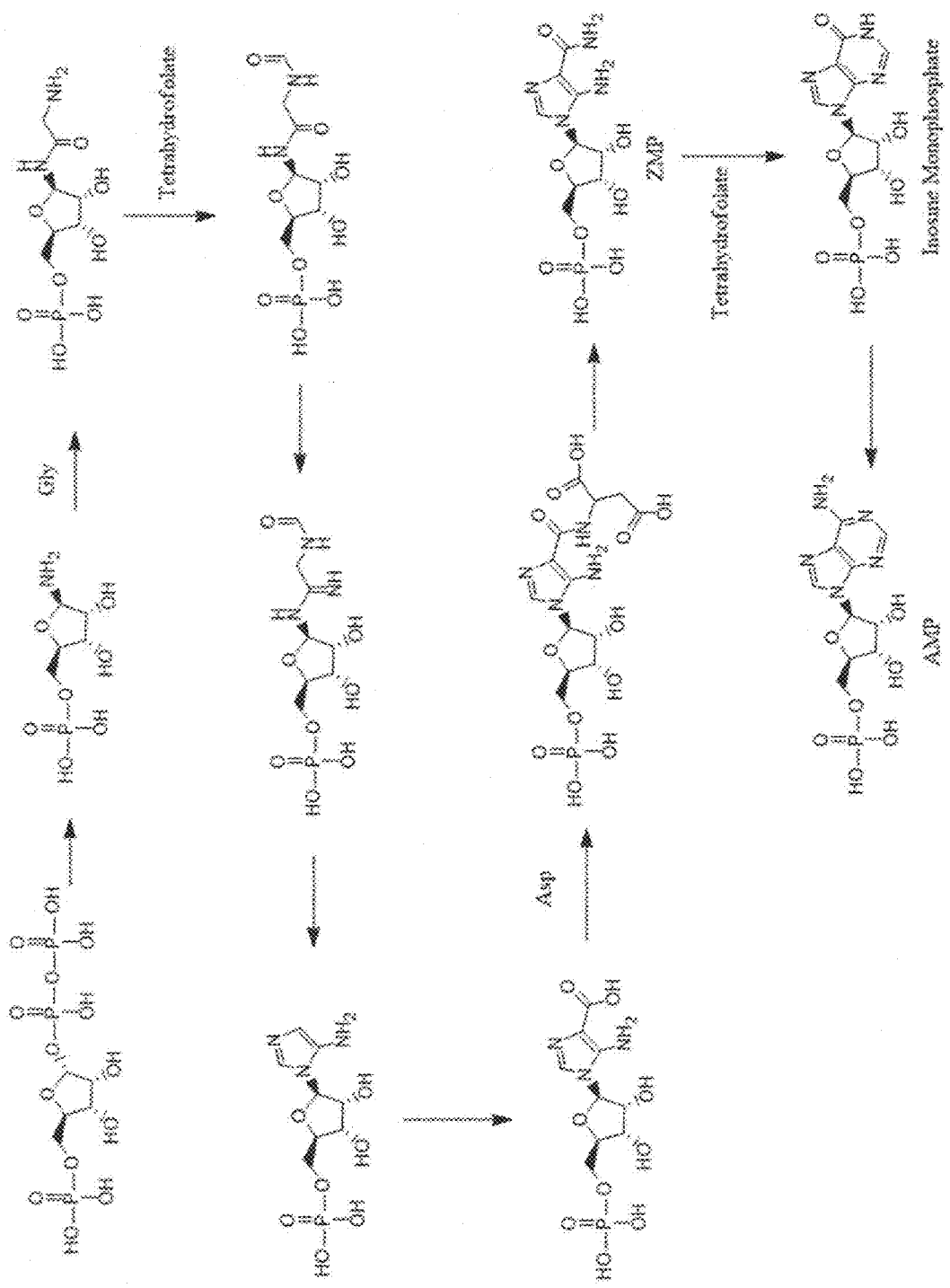
FIG. 1 depicts the de novo purine biosynthetic pathway, including ZMP and AMP.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, "a" or "an" means "at least one" or "one or more".

The term "alkyl" as used herein refers to saturated hydrocarbon groups in a straight, branched, or cyclic configuration or any combination thereof, and particularly contemplated alkyl groups include those having ten or less carbon atoms, especially 1-6 carbon atoms and lower alkyl groups having 1-4 carbon atoms. Exemplary alkyl groups are methyl, ethyl, propyl, isopropyl, butyl, sec-butyl, tertiary butyl, pentyl, isopentyl, hexyl, cyclopropylmethyl, etc.

Alkyl groups can be unsubstituted, or they can be substituted to the extent that such substitution makes sense chemically. Typical substituents include, but are not limited to, halo, =O, =N—CN, =N—OR$^a$, =NR$^a$, —OR$^a$, —NR$^a{}_2$, —SR$^a$, —SO$_2$R$^a$, —SO$_2$NR$^a{}_2$, —NR$^a$SO$_2$R$^a$, —NR$^a$CONR$^a{}_2$, —NR$^a$COOR$^a$, —NR$^a$COR$^a$, —CN, —COOR$^a$, —CONR$^a{}_2$, —OOCR$^a$, —COR$^a$, and —NO$_2$, wherein each R$^a$ is independently H, C$_1$-C$_4$ alkyl, C$_3$-C$_2$ heterocyclyl, C$_1$-C$_5$ acyl, C$_2$-C$_6$ alkenyl, C$_2$-C$_8$ alkynyl, C$_6$-C$_{10}$ aryl, or C$_5$-C$_{10}$ heteroaryl, and each R$^a$ is optionally substituted with halo, =O, =N—CN, =N—OR$^b$, =NR, OR$^b$, NR$^b{}_2$, SR$^b$, SO$_2$R$^b$, SO$_2$NR$^b{}_2$, NR$^b$SO$_2$R$^b$, NR$^b$CONR$^b{}_2$, NR$^b$COR$^b$, NR$^b$COR$^b$, CN, COOR$^b$, CONR$^b{}_2$, OOCR$^b$, COR$^b$, and NO$_2$, wherein each R$^b$ is independently H, C$_1$-C$_4$ alkyl, C$_3$-C$_7$ heterocyclyl, C$_1$-C$_5$ acyl, C$_2$-C$_6$ alkenyl, C$_2$-C$_8$ alkynyl, C$_6$-C$_{10}$ aryl, or C$_5$-C$_{10}$ heteroaryl. Where a substituent group contains two R$^a$ or R$^b$ groups on the same or adjacent atoms (e.g., —NR$^b{}_2$, or —NR$^b$—C(O)—R$^b$), the two R$^a$ or R$^b$ groups can optionally be taken together with the atoms in the substituent group to which are attached to form a ring having 5-8 ring members, which can be substituted as allowed for the R$^a$ or R$^b$ itself, and can contain an additional heteroatom (N, O or S) as a ring member.

The term "alkenyl" as used herein refers to an alkyl as defined above having at least two carbon atoms and at least one carbon-carbon double bond. Thus, particularly contemplated alkenyl groups include straight, branched, or cyclic alkenyl groups having two to ten carbon atoms (e.g., ethenyl, propenyl, butenyl, pentenyl, etc.) or 5-10 atoms for cyclic alkenyl groups. Alkenyl groups are optionally substituted by groups suitable for alkyl groups as set forth herein.

Similarly, the term "alkynyl" as used herein refers to an alkyl or alkenyl as defined above and having at least two (preferably three) carbon atoms and at least one carbon-carbon triple bond. Especially contemplated alkynyls include straight, branched, or cyclic alkynes having two to ten total carbon atoms (e.g., ethynyl, propynyl, butynyl, cyclopropylethynyl, etc.). Alkynyl groups are optionally substituted by groups suitable for alkyl groups as set forth herein.

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. Cycloalkyls can also include one or two double bonds, which form "cycloalkenyl" groups. Cycloalkyl groups are optionally substituted by groups suitable for alkyl groups as set forth herein.

The term "aryl" or "aromatic moiety" as used herein refers to an aromatic ring system. Thus, contemplated aryl groups include phenyl and naphthyl. Furthermore, contemplated aryl groups may be fused (i.e., covalently bound with 2 atoms on the first aromatic ring) with another 5- or 6-membered heteroaryl, cycloalkyl, or heterocyclic group, and are thus termed "fused aryl" or "fused aromatic".

Aromatic groups containing one or more heteroatoms (typically N, O or S) as ring members can be referred to as heteroaryl or heteroaromatic groups. Typical heteroaromatic groups include monocyclic 5-6 membered aromatic groups such as pyridyl, pyrimidyl, pyrazinyl, thienyl, furanyl, pyrrolyl, pyrazolyl, thiazolyl, oxazolyl, isothiazolyl, isoxazolyl, and imidazolyl and the fused bicyclic moieties formed by fusing one of these monocyclic groups with a phenyl ring or with any of the heteroaromatic monocyclic groups to form an 8-10 membered bicyclic group such as indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the aromatic ring systems contain 5-12 ring member atoms.

As also used herein, the terms "heterocycle" and "heterocyclic" are used to refer to any compound or radical in which a plurality of atoms form a ring via a plurality of covalent bonds, wherein the ring includes at least one atom other than a carbon atom as a ring member. Particularly contemplated heterocyclic rings include 5- and 6-membered rings with nitrogen, sulfur, or oxygen as the non-carbon ring atom or atoms, e.g., pyrrolidine, morpholine, piperidine, tetrahydrofuran, piperazine, and the like. Typically these rings contain 0-1 oxygen or sulfur atoms, at least one and typically 2-3 carbon atoms, and up to two nitrogen atoms as ring members. Further contemplated heterocycles may be fused (i.e., covalently bound with two atoms on the first heterocyclic ring) to one or two carbocyclic rings or heterocycles, and are thus termed "fused heterocycle" or "fused heterocyclic ring" or "fused heterocyclic moieties" as used herein. Where the fused ring is aromatic, these can be referred to herein as 'heteroaryl' or heteroaromatic groups.

Heterocyclic groups that are not aromatic can be substituted with groups suitable for alkyl group substituents, as set forth above, and also by $C_1$-$C_6$ alkyl groups.

Aryl and heteroaryl groups can be substituted where permitted. Suitable substituents include, but are not limited to, halo, —$OR^a$, —$NR^a_2$, —$SR^a$, —$SO_2R^a$, —$SO_2NR^a_2$, —$NR^aSO_2R^a$, —$NR^aCONR^a_2$, —$NR^aCOOR^a$, —$NR^a$-$COR^a$, —CN, —$COOR^a$, —$CONR^a_2$, —$OOCR^a$, —$COR^a$, and —$NO_2$, wherein each $R^a$ is independently H, $C_1$-$C_4$ alkyl, $C_3$-$C_7$ heterocyclyl, $C_1$-$C_5$ acyl, $C_2$-$C_6$ alkenyl, $C_2$-$C_8$ alkynyl, $C_6$-$C_{10}$ aryl, or $C_5$-$C_{10}$ heteroaryl, and each $R^a$ is optionally substituted with halo, =O, =N—CN, =N—$OR^b$, =$NR^b$, $OR^b$, $NR^b_2$, $SR^b$, $SO_2R^b$, $SO_2NR^b_2$, $NR^bSO_2R^b$, $NR^bCONR^b_2$, N $COOR^b$, N $COR^b$, CN, $COOR^b$, $CONR^b_2$, $OOCR^b$, $COR^b$, and $NO_2$, wherein each $R^b$ is independently H, $C_1$-$C_4$ alkyl, $C_3$-$C_7$ heterocyclyl, $C_1$-$C_5$ acyl, $C_2$-$C_6$ alkenyl, $C_2$-$C_8$ alkynyl, $C_6$-$C_{10}$ aryl, or $C_5$-$C_{10}$ heteroaryl. Where a substituent group contains two $R^a$ or $R^b$ groups on the same or adjacent atoms (e.g., —$NR^b_2$, or —NR—C(O)—$R^b$), the two $R^a$ or $R^b$ groups can optionally be taken together with the atoms in the substituent group to which are attached to form a ring having 5-8 ring members, which can be substituted as allowed for the $R^a$ or $R^b$ itself, and can contain an additional heteroatom (N, O or S) as a ring member.

The term "alkoxy" as used herein refers to a hydrocarbon group connected through an oxygen atom, e.g., —O-Hc, wherein the hydrocarbon portion He may have any number of carbon atoms, typically 1-10 carbon atoms, may further include a double or triple bond and may include one or two oxygen, sulfur or nitrogen atoms in the alkyl chains, and can be substituted with any of the groups disclosed herein as substituents for an alkyl group. For example, suitable alkoxy groups include methoxy, ethoxy, propyloxy, isopropoxy, methoxyethoxy, benzyloxy, allyloxy, and the like. Similarly, the term "alkylthio" refers to alkylsulfides of the general formula —S-Hc, wherein the hydrocarbon portion He is as described for alkoxy groups. For example, contemplated alkylthio groups include methylthio, ethylthio, isopropylthio, methoxyethylthio, benzylthio, allylthio, and the like.

The term 'amino' as used herein refers to the group —$NH_2$.

The term 'acyl' as used herein refers to a group of the formula —C(=O)-D, where D represents an alkyl, alkenyl, alkynyl, cycloalkyl, aryl, heteroaryl, or heterocycle as described above. Typical examples are groups wherein D is a $C_1$-$C_6$ alkyl, $C_2$-$C_6$ alkenyl or alkynyl, or phenyl, each of which is optionally substituted. In some embodiments, D can be H, Me, Et, isopropyl, propyl, butyl, $C_1$-$C_4$ alkyl optionally substituted with —OH, —OMe, or $NH_2$, phenyl, halophenyl, alkylphenyl, and the like.

The term "aryloxy" as used herein refers to an aryl group connecting to an oxygen atom, wherein the aryl group may be further substituted. For example, suitable aryloxy groups include phenyloxy, etc. Similarly, the term "arylthio" as used herein refers to an aryl group connecting to a sulfur atom, wherein the aryl group may be further substituted. For example, suitable arylthio groups include phenylthio, etc.

The hydrocarbon portion of each alkoxy, alkylthio, alkylamino, and aryloxy, etc. can be substituted as appropriate for the relevant hydrocarbon moiety.

The term "halogen" as used herein refers to fluorine, chlorine, bromine and iodine. Where present as a substituent group, halogen or halo typically refers to F or Cl or Br, more typically F or Cl.

The term "haloalkyl" refers to an alkyl group as described above, wherein one or more hydrogen atoms on the alkyl group have been substituted with a halo group. Examples of such groups include, without limitation, fluoroalkyl groups, such as fluoroethyl, trifluoromethyl, difluoromethyl, trifluoroethyl and the like.

The term "haloalkoxy" refers to the group —O-haloalkyl and include, by way of example, groups such as trifluoromethoxy, and the like.

The term "substituted" as used herein refers to a replacement of a hydrogen atom of the unsubstituted group with at least one suitable substituent as described herein. Moreover, the term "substituted" also includes multiple degrees of substitution, and where multiple substituents are disclosed or claimed, the substituted compound can be independently substituted by one or more of the disclosed or claimed substituent moieties.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical or chemically unstable in an aqueous environment and/or synthetically non-feasible. In addition, the subject compounds include all stereochemical isomers arising from the substitution of these compounds, unless a specific isomer is disclosed. Where nucleoside analogs are disclosed, the structures represent the specific enantiomer depicted unless a mixture is indicated.

The term "pharmaceutically acceptable salt" means a salt which is acceptable for administration to a patient, such as a mammal, especially a human (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, many of which are well known in the art. These salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" refers to a compound formed when a neutral organic compound is protonated or deprotonated to produce an ionic organic moiety that is associated with an oppositely-charged counterion. For example, this may refer to a salt formed when a proton of an acidic organic molecule is replaced by a cation, such as a metal cation or an organic cation. As another example, salts of the present compounds include those wherein the compound is protonated by an inorganic or organic acid to form a cation, with the conjugate base of the inorganic or organic acid as the anionic component of the salt. Where applicable, the salt is a pharmaceutically acceptable salt, although this is not required for salts of compounds that are not intended for administration to a patient, such as precursors to the final drug compound or intermediates useful for synthesis of a compound of Formula (I).

The compounds and compositions described herein can be administered to a subject in need of treatment for any of the conditions disclosed above. The subject is typically a mammal diagnosed as being in need of treatment for one or more of such disorders, and preferably the subject is a human. The methods comprise administering an effective amount of at least one compound of Formula (I), optionally in the form of a pharmaceutical composition. Optionally, the compound may be administered in combination with one or more additional therapeutic agents, particularly therapeutic agents useful for treating the condition afflicting the particular subject.

Exemplary Embodiments

The following enumerated embodiments are representative of the invention:

In some embodiments, the present disclosure provides compound SB00039, compound 5 or compound 7, and the pharmaceutically acceptable salts thereof, and methods of treatment and pharmaceutical compositions using these compounds.

Pharmaceutical Compositions

The compounds of the invention can be prepared and administered as pharmaceutical compositions comprising a compound of Formula (I) admixed with at least one pharmaceutically acceptable carrier or excipient. In some embodiments, the pharmaceutical composition comprises at least two pharmaceutically acceptable carrier or excipient components. Suitable carriers include water, optionally buffered such as with a phosphate, carbonate, acetate, or similar buffering agent, and potentially also at least one solvating component such as a co-solvent or cyclodextrin. Suitable carriers are disclosed in the following formulations.

In some embodiments, the compounds of Formula (I) are provided in a form suitable for dissolution or suspension in an acceptable intravenous form, thus compounds of Formula (I) may be combined with one or more carrier or excipient components, and optionally then lyophilized or otherwise concentrated to a form that can readily be reconstituted with an aqueous carrier such as saline, phosphate-buffered saline, glucose, lactate or Ringer's lactate, typically at an isotonic concentration level, for intravenous administration, including infusion.

Formulations

Any suitable formulation of the compounds described herein can be prepared. See generally, *Remington's Pharmaceutical Sciences*, (2000) Hoover, J. E. editor, 20th edition, *Lippincott Williams and* Wilkins Publishing Company, Easton, Pa., pages 780-857. A formulation is selected to be suitable for an appropriate route of administration. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts of carboxylic acids also are made.

Where compounds of Formula (I) are administered in a pharmacological composition, it is contemplated that the compounds can be formulated in admixture with a pharmaceutically acceptable excipient and/or carrier. For example, contemplated compounds can be administered orally as neutral compounds or as pharmaceutically acceptable salts, or intravenously in a physiological saline solution or similar suitable isotonic solution. Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

The compounds of Formula I as described herein are generally soluble in organic solvents such as chloroform, dichloromethane, ethyl acetate, ethanol, methanol, isopropanol, acetonitrile, glycerol, N,N-dimethylformamide, N,N-dimetheylaceatmide, dimethylsulfoxide, etc. In one embodiment, the present invention provides formulations prepared by mixing a compound of Formula I with a pharmaceutically acceptable carrier. In one aspect, the formulation may be prepared using a method comprising: a) dissolving a described compound in a water-soluble organic solvent, a non-ionic solvent, a water-soluble lipid, a cyclodextrin, a vitamin such as tocopherol, a fatty acid, a fatty acid ester, a phospholipid, or a combination thereof, to provide a solution; and b) adding saline or a buffer containing 1-10% carbohydrate solution. In one example, the carbohydrate comprises dextrose. The pharmaceutical compositions obtained using the present methods are stable and useful for animal and clinical applications.

Illustrative examples of water soluble organic solvents for use in the present compositions and methods include and are not limited to polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of alcohols include but are not limited to methanol, ethanol, isopropanol, glycerol, or propylene glycol.

Illustrative examples of water soluble non-ionic surfactants for use in the present methods and compositions include and are not limited to CREMOPHOR® EL, polyethylene glycol modified CREMOPHOR® (polyoxyethyleneglyceroltriricinoleat 35), hydrogenated CREMOPHOR® RH40, hydrogenated CREMOPHOR® RH60, PEG-succinate, polysorbate 20, polysorbate 80, SOLUTOL® HS (polyethylene glycol 660 12-hydroxystearate), sorbitan monooleate, poloxamer, LABRAFIL® (ethoxylated persic oil), LABRASOL® (capryl-caproyl macrogol-8-glyceride), GELUCIRE® (glycerol ester), SOFTIGEN® (PEG 6 caprylic glyceride), glycerin, glycol-polysorbate, or a combination thereof.

Illustrative examples of water soluble lipids for use in the present methods and compositions include but are not limited to vegetable oils, triglycerides, plant oils, or a combination thereof. Examples of lipid oils include but are not limited to castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Illustrative examples of fatty acids and fatty acid esters for use in the present methods and compositions include but are not limited to oleic acid, monoglycerides, diglycerides, a mono- or di-fatty acid ester of PEG, or a combination thereof. Illustrative examples of cyclodextrins for use in the present methods include but are not limited to alpha-cyclodextrin, beta-cyclodextrin, hydroxypropyl-beta-cyclodextrin, or sulfobutyl ether-beta-cyclodextrin.

Illustrative examples of phospholipids for use in the present methods and compositions include but are not limited to soy phosphatidylcholine, or distearoyl phosphatidylglycerol, and hydrogenated forms thereof, or a combination thereof.

In addition to carriers useful in the pharmaceutical compositions of the invention, compounds may be admixed with excipients beneficial to solubilize, stabilize, or otherwise modify the compound of Formula (I) to provide a suitable formulated composition for storage or administration. Excipients include colorants, flavoring agents, stabilizers, disintegrants, glidants, lubricants, preservatives and the like.

In many embodiments, the compounds of Formula (I) are formulated as solutions, emulsions, dispersions, or suspensions that are suitable for injection or infusion, or formulated so they can readily be diluted for intravenous administration or infusion.

One of ordinary skill in the art may modify the formulations within the teachings of the specification to provide numerous formulations for a particular route of administration. In particular, the compounds may be modified to render them more soluble in water or other carriers, often using solvating agents disclosed above, particularly ones that are known in the art to be pharmaceutically acceptable and suited for administration via injection or infusion. It is also well within the ordinary skill of the art to select or modify the route of administration and dosage regimen of a particular compound in order to manage the pharmacokinetics of the present compounds for maximum beneficial effect in a patient.

Drug Combinations

The methods of using compounds of Formula (I) comprise administering an effective amount of at least one exemplary compound of Formula (I); optionally the compound may be administered in combination with one or more additional therapeutic agents, particularly at least one therapeutic agent that is useful for treatment of the same condition for which the compound of Formula (I) is indicated, or treatment of symptoms or complications of this condition, or reduction of side effects associated with treatment of this condition.

The additional therapeutic agent(s) may be administered in a separate pharmaceutical composition from the compound of Formula (I), or may be included with the compound of the present disclosure in a single pharmaceutical composition. The additional therapeutic agent may be administered simultaneously with, prior to, or after administration of the compound(s) of Formula (I) according to the present disclosure.

Methods of Using Compounds of Formula (I) and Pharmaceutical Compositions Thereof The present invention provides pharmaceutical compositions for the treatment and/or prevention of conditions described herein, and methods of using these compounds and compositions containing a compound of Formula I as described herein. The methods typically comprise administering the compound or composition to a subject, typically a human. In some embodiments, the method is for treatment and the subject is one already having been diagnosed as in need of such treatment for a condition selected from those described herein. Preferably, the compound or composition is administered in an amount effective to treat the subject's condition. Selection of a suitable compound of Formula (I), and suitable formulation thereof, and suitable routes of administration and dosage therefor are within the ordinary level of skill in the art in view of the disclosures provided herein and conventional testing, treatment and monitoring practices. For solubility reasons, the compound of Formula I is frequently formulated and administered as a pharmaceutically acceptable salt.

To practice the method of the present invention, compounds having formula (I) and pharmaceutical compositions thereof may be administered orally, parenterally, by inhalation, topically, rectally, nasally, buccally, vaginally, via an implanted reservoir, or other drug administration methods. Typically, compounds of Formula (I) are administered by parenteral routes. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. A preferred route of administration for compounds of Formula (I) is intravenous injection or intravenous infusion, commonly in a solution or suspension comprising a typical IV fluid such as isotonic saline or isotonic glucose solution or Ringer's lactate.

Suitable carriers and other pharmaceutical composition components are typically sterile. A sterile injectable composition, such as a sterile injectable aqueous or oleaginous suspension, may be formulated according to techniques known in the art using suitable dispersing or wetting agents and suspending agents as needed. The sterile injectable preparation may also be a sterile injectable solution or suspension in a non-toxic parenterally acceptable diluent or solvent. Among the acceptable vehicles and solvents that may be employed include mannitol, dextrose, citrate buffer, water, Ringer's solution and isotonic sodium chloride solution.

In addition, sterile, fixed oils are conventionally employed as a solvent or suspending medium (e.g., synthetic mono- or diglycerides). Fatty acids, such as oleic acid and its glyceride derivatives, are useful in the preparation of injectables, as are pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Various emulsifying agents or bioavailability enhancers which are commonly used in the manufacture of pharmaceutically acceptable solid, liquid, or other dosage forms can also be used for the purpose of formulation.

A composition for oral administration may be any orally acceptable dosage form including, but not limited to, tablets, capsules, emulsions and aqueous suspensions, dispersions and solutions. In the case of tablets for oral use, commonly used carriers include lactose and corn starch. Lubricating agents, such as magnesium stearate, can also be added. For oral administration in a capsule form, useful diluents include lactose and dried corn starch. When aqueous suspensions or emulsions are administered orally, the active ingredient can be suspended or dissolved in an oily phase combined with emulsifying or suspending agents. If needed, certain sweetening, flavoring, or coloring agents can be added. A nasal aerosol or inhalation compositions can be prepared according to techniques well-known in the art of pharmaceutical formulation and can be prepared as solutions in, for example saline, employing suitable preservatives (for example, benzyl alcohol), absorption promoters to enhance bioavailability, and/or other solubilizing or dispersing agents known in the art.

Synthesis of Compounds of Formula (I)

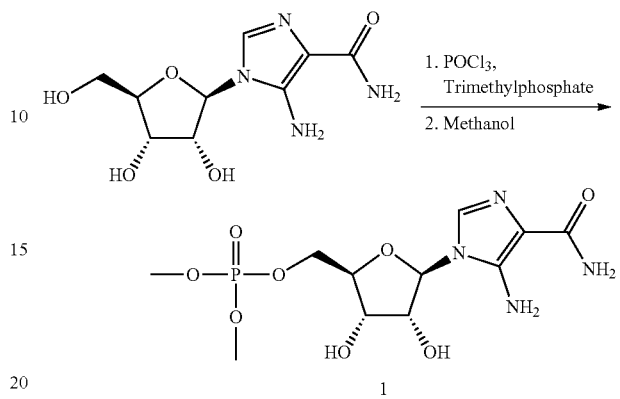

Compound 1: The starting nucleoside was (0.166 g, 0.643 mmol) was suspended in trimethylphosphate (3 ml). With stirring under nitrogen, neat phosphorous oxychloride (0.359 ml, 3.86 mmol) was added. The reaction was stirred for 2 hours at room temperature. Methanol (0.500 ml, 12 mmol) was then added and the reaction was stirred for 30 minutes at room temperature. Triethylamine (2 ml, 15 mmol), was carefully added to quench. The reaction was diluted with acetonitrile 40 ml and loaded onto a silica gel column. The desired product was eluted using a gradient of 0 to 30% methanol in acetonitrile. (0.075 g, 32%) ([M+1], 367)

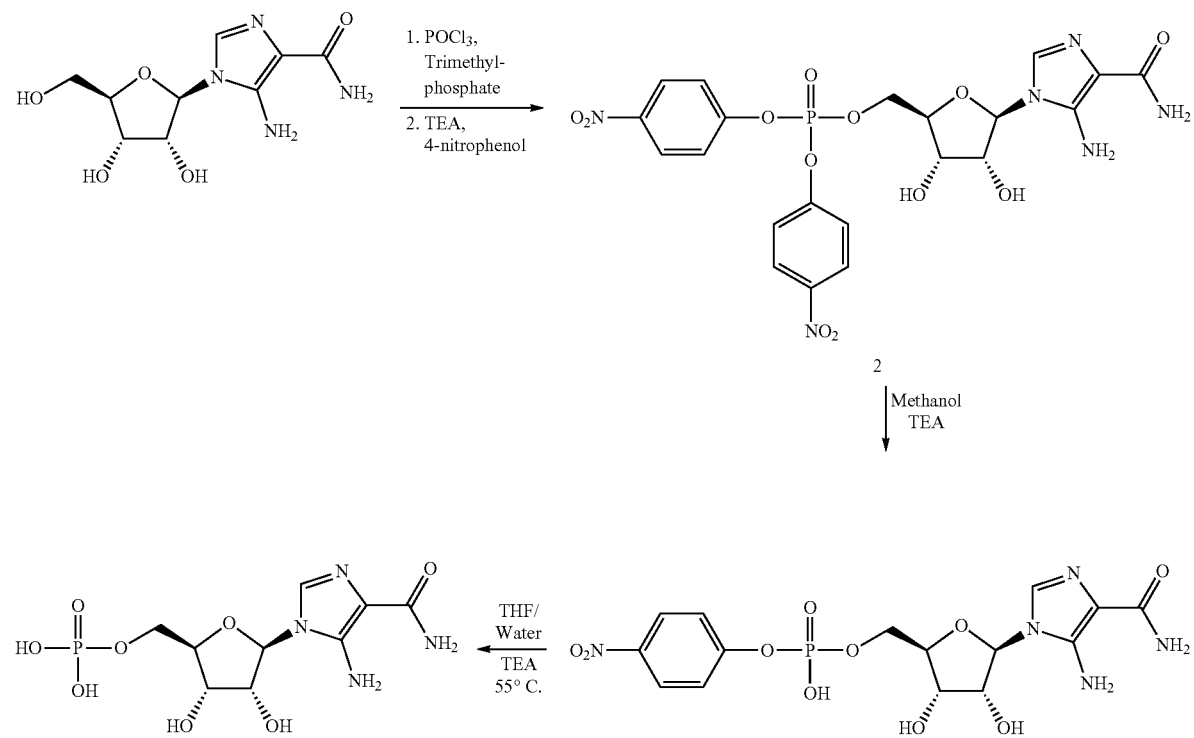

Compound 2: The starting nucleoside (0.155 g, 0.6 mmol) was suspended in trimethylphosphate (3 ml). With stirring under nitrogen, phosphorous oxychloride (0.335 ml, 3.6 mmol) was added neat. The reaction was stirred for 2 hours at room temperature. 4-nitrophenol (2.085 g, 15 mmol) was then added and the reaction was stirred for 30 minutes at room temperature. Triethylamine (15 mmol, 2 ml) was carefully added to quench. The reaction was diluted with ethyl acetate (30 ml) and loaded onto a silica gel column. The desired product was eluted using a gradient of 0 to 10% methanol in ethyl acetate. (0.174 g, 50%) ([M+1], 581)

Compound 3: The starting di-(nitrophenyl) phosphate nucleoside (0.100 g, 0.17 mmol) was dissolved in methanol (15 ml). With stirring under nitrogen, triethylamine (0.117 ml, 0.85 mmol) was added neat. The reaction was stirred for 3 hours at room temperature. Acetic acid (0.120 ml, 2 mmol) was added to quench. Solvents were removed by rotary evaporation. The residue was dissolved in DCM and loaded onto a silica gel column. The desired product was eluted using a gradient of 0 to 20% methanol in ethyl acetate. (0.035 g, 43%) ([M+1], 474)

Compound 4: The starting nitrophenylmethyl phosphate nucleoside (0.025 g, 0.05 mmol) was dissolved in a 1:1 mixture of THF and water (5 ml). With stirring under nitrogen, triethylamine (0.034 ml, 0.25 mmol) was added neat. The reaction was heated to 55° C. and stirred for 2 hours. Acetic acid (0.050 ml, 0.8 mmol) was added to quench. Solvents were removed by rotary evaporation. The desired product was purified by prep hplc (0.007 g, 40%) ([M+1], 353)

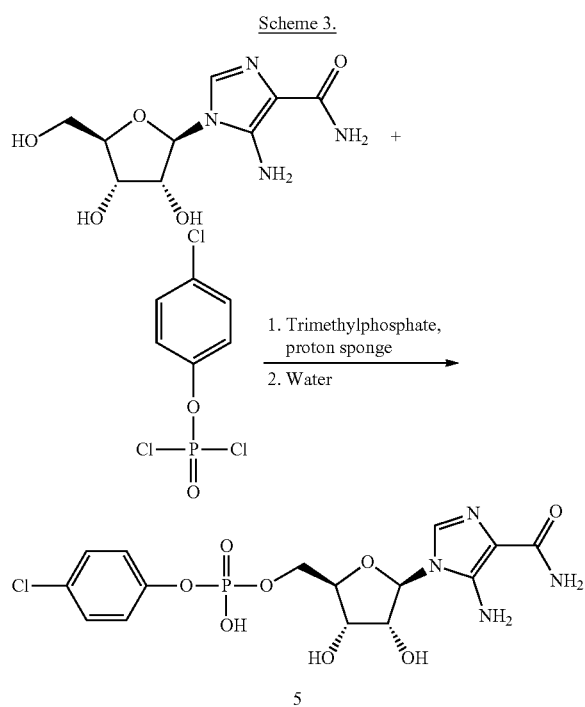

Scheme 3.

Compound 5: The starting nucleoside (0.100 g, 0.39 mmol) was suspended in trimethylphosphate (3 ml). With stirring under nitrogen, proton sponge (0.332 g, 1.55 mmol) was added. The reaction was stirred for 10 minutes at room temperature and then 4-chlorophenylphosphorodichloridate (0.252 ml, 1.55 mmol) was added neat. The reaction was stirred for 1 hour at room temperature. Water (1 ml) was then added and the reaction was stirred for 30 minutes at room temperature. Triethylamine (10 mmol, 2 ml) was carefully added to quench. The reaction was diluted with acetonitrile (30 ml) and loaded onto a silica gel column. The desired product was eluted using a gradient of 0 to 30% methanol in acetonitrile. (0.070 g, 40%) ([M+1], 449)

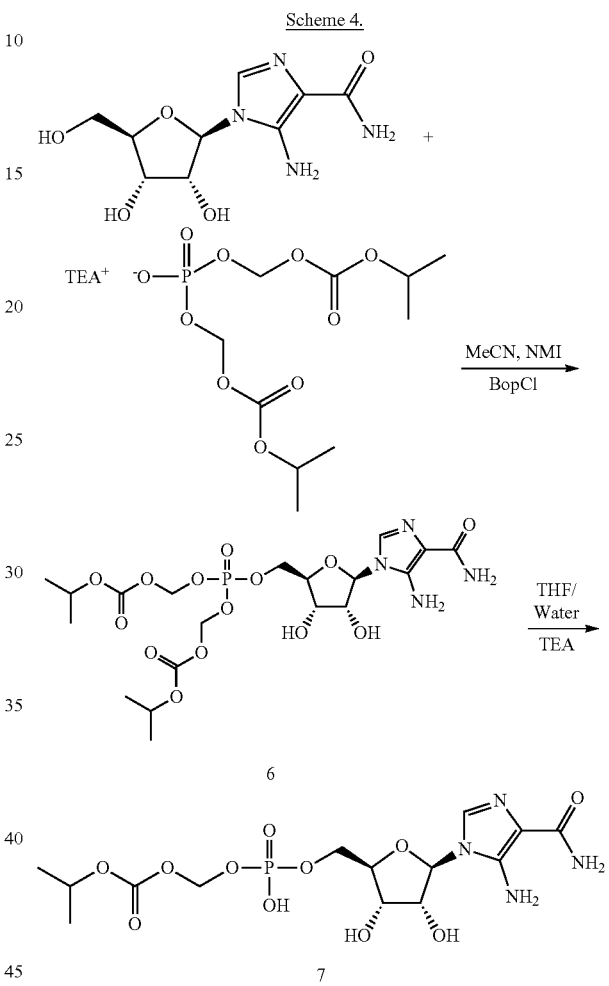

Scheme 4.

Compound 6: The starting nucleoside (0.204 g, 0.79 mmol) and the phosphate TEA salt (0.514 g, 1.58 mmol) were suspended in acetonitrile (10 ml). With stirring under nitrogen, 1-methylimidazole (0.314 ml, 3.95 mmol) was added. The reaction was stirred for 10 minutes at room temperature and then bis(2-oxo-3-oxazolidinyl)phosphinic chloride (0.402 g, 1.58 mmol) was added. The reaction was stirred for 1 hour at room temperature then additional bis(2-oxo-3-oxazolidinyl)phosphinic chloride (0.804 g, 3.16 mmol) was added. The reaction was stirred for 2 hours. When the reaction was complete by LC/MS, solvents were removed by rotary evaporation. The desired product was purified by preparatory HPLC. (0.075 g, 17%) ([M+1], 571)

Compound 7: The starting poc phosphate nucleoside (0.050 g, 0.09 mmol) was dissolved in a 1:1 mixture of THF and water (4 ml). With stirring under nitrogen, triethylamine (0.027 ml, 0.2 mmol) was added neat. The reaction was stirred for 1 hour at room temperature. When the reaction was complete by LC/MS, acetic acid (0.100 ml, 1.7 mmol)

was added to quench. Solvents were removed by rotary evaporation. The desired product was purified by prep hplc (0.013 g, 32%) ([M+1], 455)

Biological Activity of Compounds of Formula (I)

Some exemplary assays and examples for assessing therapeutic efficacy, e.g., anticancer effects, of exemplary compounds of the invention are described herein or well known in the art. HEK293 is a human kidney cell line, and efficacy on HEK293 is considered to be predictive of usefulness for therapeutic treatment. In the Figures below, the activity of the compounds on HEK293 cells according to the method described below is reported as the CC50, or 50% cytotoxic concentration (micromolar).

FIG. 1. Activity of SB00039 on HEK293 cells.

The first two structures above are the known compounds AICAR and ZMP. The third structure (SB00024) is an uncleavable analogue of ZMP (one not expected to readily cleave in vivo), and was inactive at 500 uM. The fourth structure (SB00039) is an exemplary prodrug of Formula I, and exhibits roughly 100 times the potency of AICAR. The final structure (SB00038) is the byproduct of the unmasking of the prodrug. This was tested to show that the potency of SB00039 comes from the prodrug penetrating the cell and being unmasked to produce ZMP, and not from the byproduct.

Figure 2:
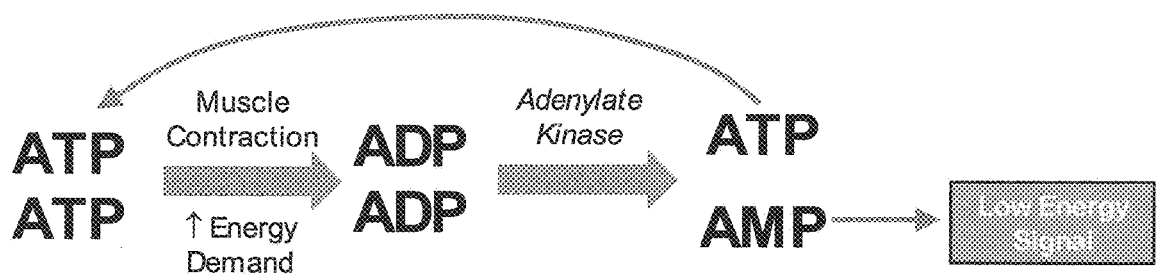
FIG. 2 depicts energy demand driving production of AMP. When the cell requires more energy, ATP is quickly broken down into ADP. Adenylate kinase is an enzyme that transfers a phosphate from one ADP to another, thus synthesizing one ATP and one AMP. The ATP can be used for continued energy demands of the cell, while the AMP molecule acts as a low-energy signal to other cellular enzymes.
Figure 3:
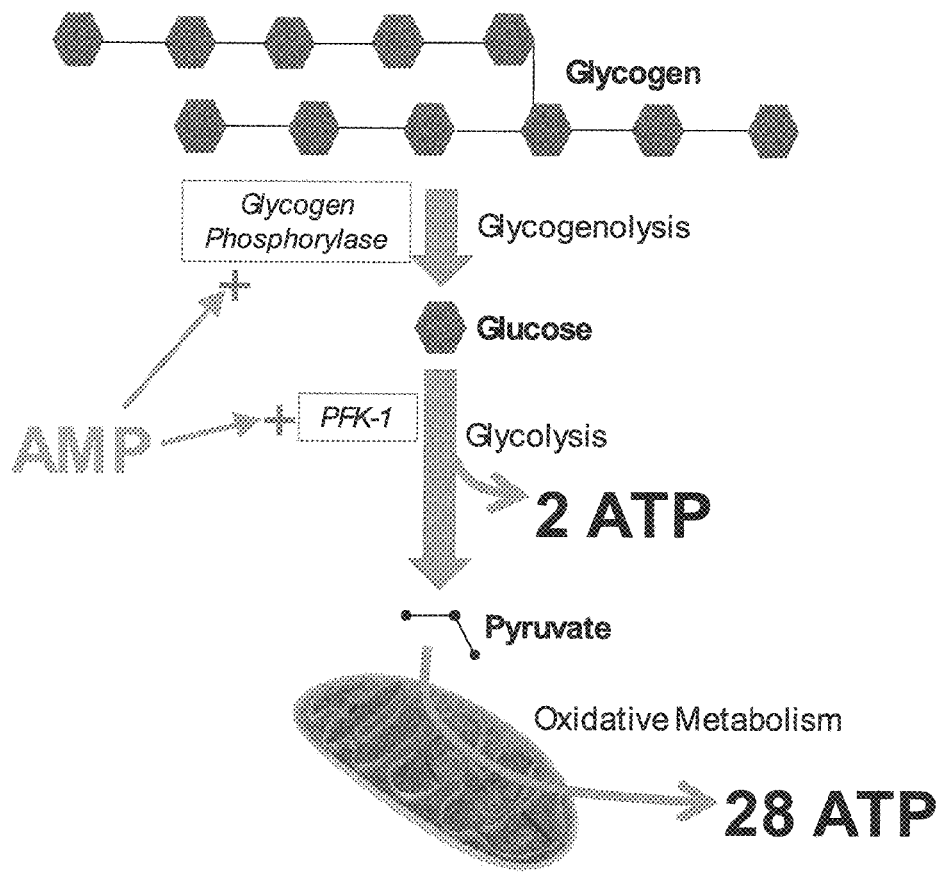
FIG. 3 illustrates AMP stimulation of glycolysis and ATP production. When the cell requires more energy, ATP breakdown, and AMP production both increase. AMP activates two key enzymes that mobilize stored glucose and promote glycolysis (the breakdown of glucose). This potentially increases ATP production, which can be used to fuel the energy needs of the cell.
Figure 4:
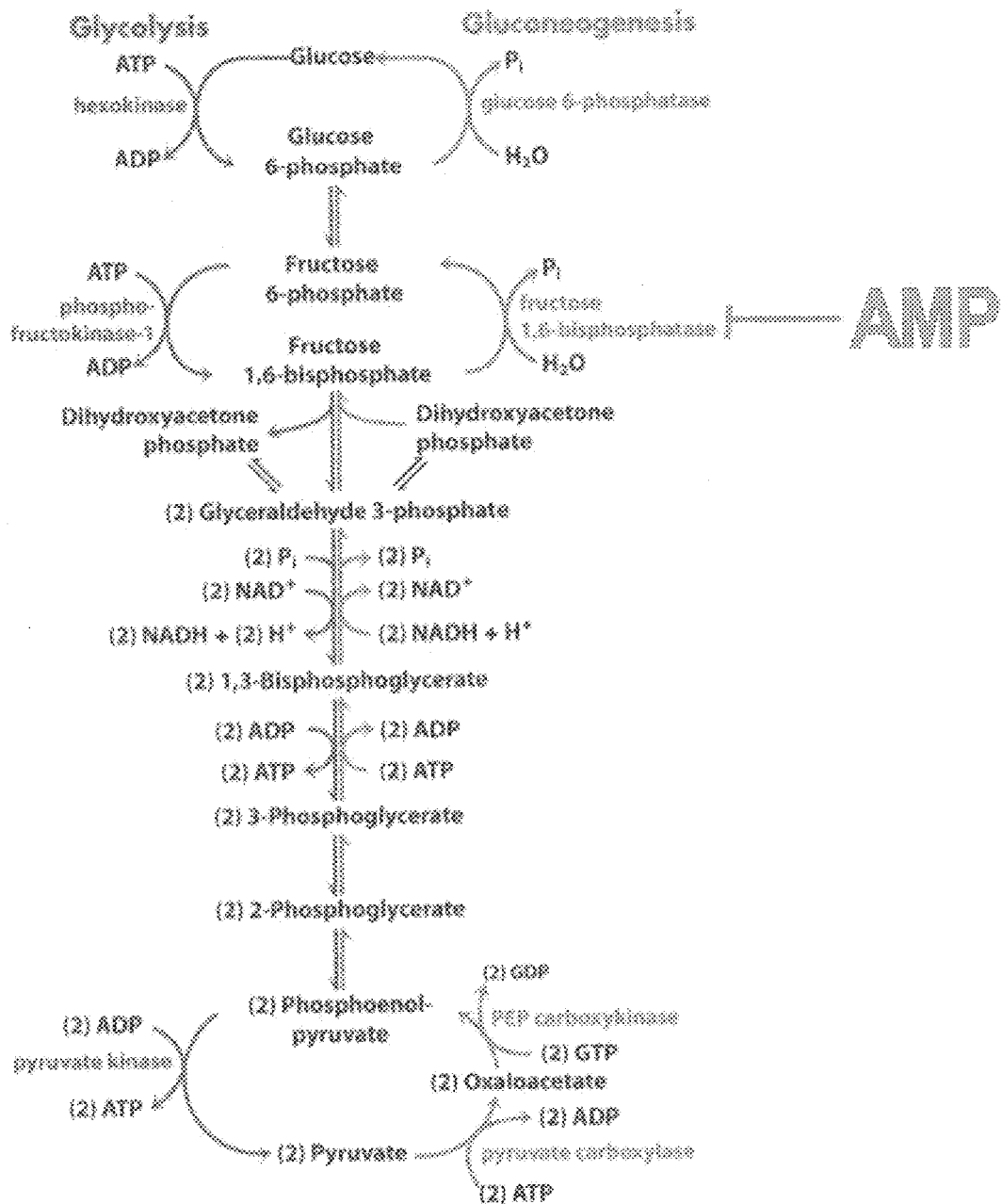
FIG. 4 illustrates the fructose-1,6-bisphosphatase role in gluconeogenesis. Fructose bisphosphatase catalyses the conversion of fructose-1,6-bisphosphate to fructose-6-phosphate, which is the reverse of the reaction that is catalysed by phosphofructokinase in glycolysis.

The potency of SM00039 is surprising, because other prodrugs of ZMP did not exhibit improved potency. FIG. 2 shows a number of other prodrugs of ZMP that did not enhance its potency in the HEK239 assay.

FIG. 2. Prodrugs of ZMP that did not enhance efficacy on HEK2.

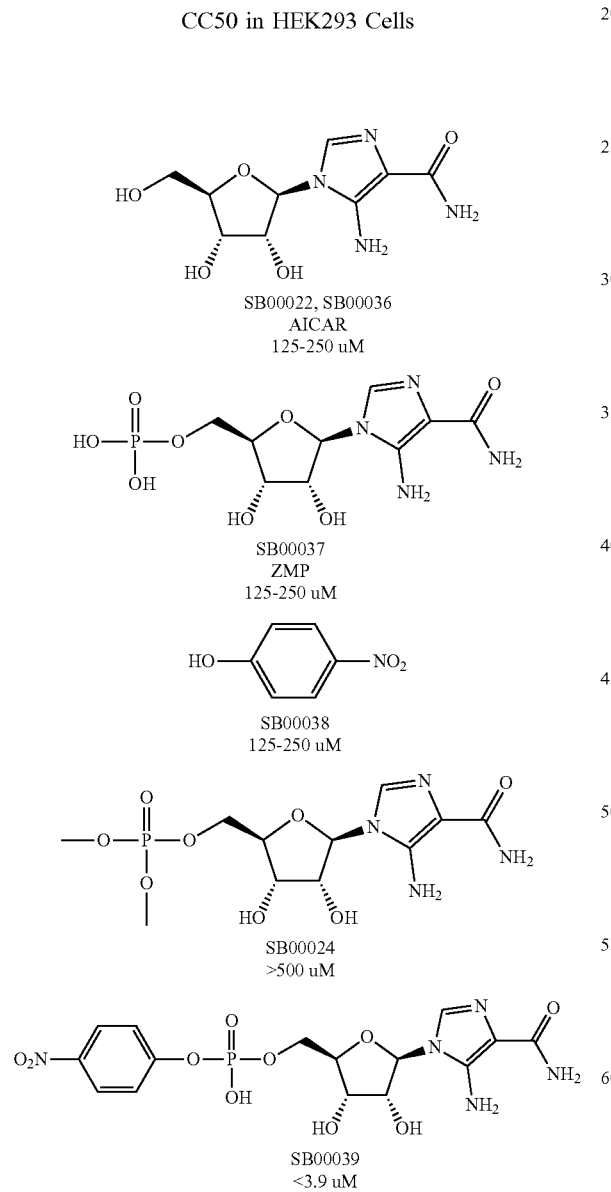

CC50 in HEK293 Cells

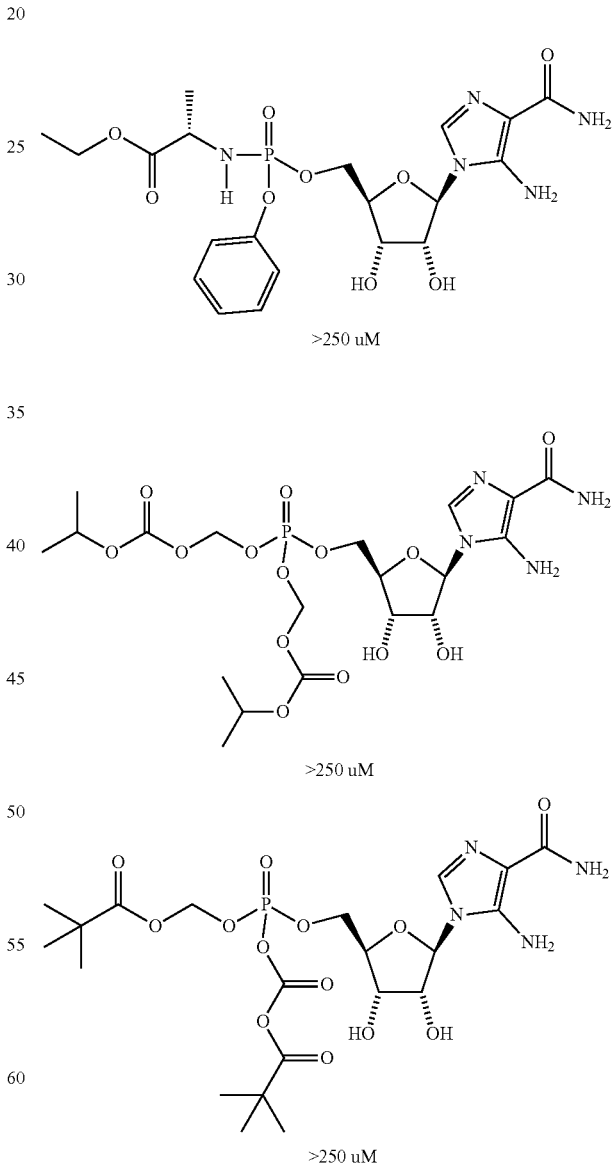

A few ZMP prodrugs have been reported in the literature, but they also do not show efficacy in the HEK293 assay.

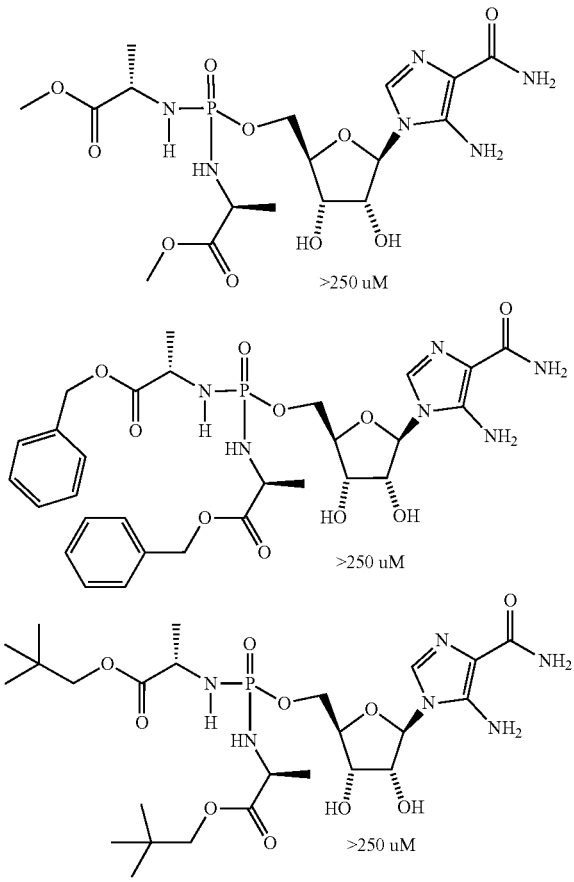

McGuigan, *Eur. J. Med. Chem.* 70, 326-40 (2013).

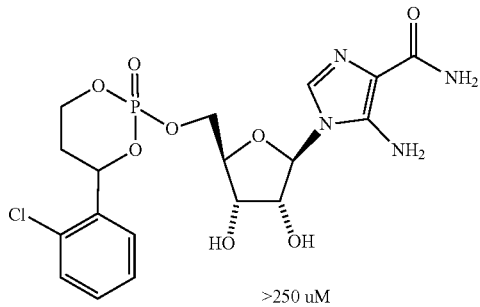 [SMILES: NC(=O)c1ncn([C@@H]2O[C@H](COP3(=O)OCCC(c4ccccc4Cl)O3)[C@@H](O)[C@H]2O)c1N]

Bookser, et. al, *J. Combinatorial Chem.* 10(4), 567-72 (2008).

Material and Methods

Cell Culture and Reagents

HEK293 cells were obtained from American Type Culture Collection (ATCC) (Rockville Maryland). Cells were maintained in Dulbecco's modified Eagle's medium (DMEM) (Invitrogen, Carlsbad, CA) with 10% fetal bovine serum (FBS), 10 mM HEPES and 1 mM sodium pyruvate. Cells were grown at 37° C. in a humidified incubator with a gas phase of 5% $C_{O2}$. Cells were grown for 24 hours in a Tripleflask (NUNC) to ~95% confluence and then resuspended for dispensing at 125,000 cells/mL of DMEM, 10% FBS, 10 mM Hepes and 1 mM sodium pyruvate.

HEK293 Cytotoxicity Assay

HEK293 cells were seeded in 96 well microtiter plates at 10000 cells/well. After 24 hours of incubation an equal volume of fresh media containing test compounds at given concentrations was added. Plates were then incubated and cells were allowed to proliferate for 48 hours at 37° C., 95% humidity, and 5% $C_{O2}$. At 72 hours, plates were removed from the incubator and cooled for 15 minutes to room temperature. A solution of Promega CellTiterGlo (100 microliters) was added by Thermo Combi and the plates were allowed to sit for 10 minutes before reading on a Perkin-Elmer EnVision with US LUM settings for 0.1 sec per well. The 50% cytotoxicity concentration (CC50) was defined as the compound concentration required to reduce the viable cells by 50%.

The detailed description set forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

The invention claimed is:

1. A method to treat a muscle disorder, wherein the method comprises administering a compound of the formula

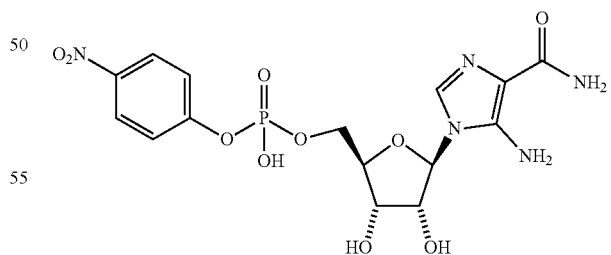

or a pharmaceutically acceptable salt thereof to a subject in need of such treatment.

2. The method of claim 1, wherein the condition is a muscle disorder selected from polymyositis, dermatomyositis, muscular dystrophy, myasthenia gravis, amyotrophic lateral sclerosis rhabdomyolysis, and cardiomyopathy.

3. The method of claim 1, wherein the condition is muscular dystrophy.

4. The method of claim 2, wherein the muscle condition is polymyositis.

5. The method of claim 2, wherein the muscle condition is myasthenia gravis.

6. The method of claim 2, wherein the muscle condition is amyotrophic lateral sclerosis.

7. The method of claim 2, wherein the muscle condition is rhabdomyolysis.

8. The method of claim 2, wherein the muscle condition is cardiomyopathy.

9. A method to activate fructose-1,6-bisphosphatase, glycogen phosphorylase, or phosphofructokinase-1 in a cell, which comprises contacting the cell with a compound according to claim 1.

10. A method to treat a condition selected from diabetes, leukemia and lymphoma, which comprises administering a compound of the formula

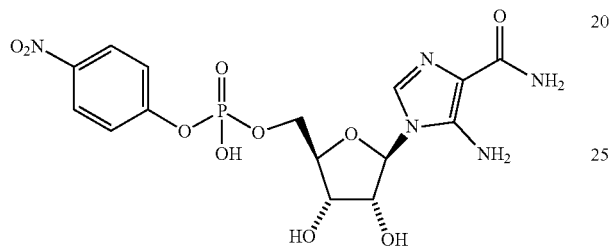

or a pharmaceutically acceptable salt thereof to a subject in need of such treatment.

* * * * *